(12) United States Patent
Fujii et al.

(10) Patent No.: US 9,011,678 B2
(45) Date of Patent: Apr. 21, 2015

(54) BLOOD PURIFICATION APPARATUS AND BLOOD PURIFICATION CIRCUIT

(75) Inventors: Junya Fujii, Hiroshima (JP); Shigeki Kawarabata, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 596 days.

(21) Appl. No.: 12/278,427

(22) PCT Filed: Jan. 29, 2007

(86) PCT No.: PCT/JP2007/051344
§ 371 (c)(1),
(2), (4) Date: Aug. 6, 2008

(87) PCT Pub. No.: WO2007/091438
PCT Pub. Date: Aug. 16, 2007

(65) Prior Publication Data
US 2009/0272679 A1  Nov. 5, 2009

(30) Foreign Application Priority Data

Feb. 7, 2006 (JP) ................................. 2006-030238
Feb. 7, 2006 (JP) ................................. 2006-030239

(51) Int. Cl.
*B01D 29/60* (2006.01)
*A61M 1/16* (2006.01)
*A61M 1/34* (2006.01)

(52) U.S. Cl.
CPC ............... *A61M 1/16* (2013.01); *A61M 1/3441* (2013.01); *A61M 1/3437* (2014.02)

(58) Field of Classification Search
None
See application file for complete search history.

(56) References Cited

U.S. PATENT DOCUMENTS 4,711,715 A    12/1987  Polaschegg
4,728,433 A     3/1988  Buck et al.
(Continued)

FOREIGN PATENT DOCUMENTS

CN    1404883    3/2003
DE    4240681    6/1994
(Continued)

OTHER PUBLICATIONS

English language Abstract of WO 2004/014463 A1; Feb. 19, 2004.
(Continued)

*Primary Examiner* — Dirk Bass
(74) *Attorney, Agent, or Firm* — Greenblum & Bernstein, P.L.C.

(57) ABSTRACT

The present invention provides a blood purification apparatus and a blood purification circuit, by which a circuit can be shared by different modes for performing respective continuous blood purification methods, a structure of the apparatus performing the continuous blood purification methods can be simplified, and CHF, CHD, CHDF, and ECUM can be performed. The blood purification apparatus and the blood purification circuit according to the present invention includes: a first supply fluid channel (3) having one end connected to a supply fluid container (1) containing a supply fluid flowing in the first supply fluid channel (3); a first branched part (4) connected to the other end of the first supply fluid channel (3); a first supply fluid pump (10a) connected to the first branched part (4); a second supply fluid channel (7) which has one end connected to the first supply fluid pump (10a) and the other end connected to a dialyzer (6) that filters and dialyzes blood, and in which the supply fluid from the first supply fluid pump (10a) flows; a second supply fluid pump (10b) connected to the first branched part (4); and a third supply fluid channel (9) in which a supply fluid from the second supply fluid pump (10b) flows, having one end connected to the second supply fluid pump (10b) and the other end connected to a vein side blood channel (16) in which blood taken from a patient flows.

11 Claims, 5 Drawing Sheets

(56) References Cited

U.S. PATENT DOCUMENTS

| | | | |
|---|---|---|---|
| 5,114,580 A * | 5/1992 | Ahmad et al. | 210/646 |
| 5,366,630 A * | 11/1994 | Chevallet | 210/645 |
| 5,578,223 A | 11/1996 | Bene et al. | |
| 5,698,090 A | 12/1997 | Bene et al. | |
| 5,702,597 A | 12/1997 | Chevallet et al. | |
| 5,725,775 A | 3/1998 | Bene et al. | |
| 2003/0032914 A1 | 2/2003 | Inoue et al. | |
| 2005/0000868 A1 | 1/2005 | Weigel et al. | |
| 2006/0124548 A1 * | 6/2006 | Okazaki | 210/646 |

FOREIGN PATENT DOCUMENTS

| | | |
|---|---|---|
| DE | 69532258 | 9/2004 |
| EP | 0122604 | 10/1984 |
| EP | 0678301 | 10/1995 |
| EP | 0694312 | 1/1996 |
| EP | 0722744 A1 | 7/1996 |
| EP | 1175917 | 1/2002 |
| EP | 1543853 A1 | 6/2005 |
| EP | 1200141 | 9/2005 |
| JP | 63-234974 | 9/1988 |
| JP | 3-215270 | 9/1991 |
| JP | 5-168703 A | 7/1993 |
| JP | 6-233813 | 8/1994 |
| JP | 8-66474 | 3/1996 |
| JP | 9-239024 | 9/1997 |
| JP | 2000-107281 | 4/2000 |
| JP | 2001-541 | 1/2001 |
| JP | 3180309 | 4/2001 |
| JP | 3180309 B2 | 4/2001 |
| JP | 2004-524083 | 8/2004 |
| JP | 2004-524083 A | 8/2004 |
| JP | 2004-313303 | 11/2004 |
| JP | 3714947 | 9/2005 |
| JP | 3714947 B2 | 9/2005 |
| WO | 01/76661 | 10/2001 |
| WO | 02/062454 A1 | 8/2002 |
| WO | 2004/066121 | 8/2004 |
| WO | 2004/069311 | 8/2004 |

OTHER PUBLICATIONS

English language Abstract of JP 8-191889 A; Jul. 30, 1996.
English language Abstract of JP 5-168703 A; Jul. 2, 1993.
China Office action, dated Feb. 28, 2013.
Instructions for Use Automatic Acute Balance Monitor AQUARIUS Edward Lifescience; May 2004, German Ver.4, Rev. A (2004), along with an English-language translation thereof.
Instructions for Use Automatic Acute Balance Monitor AQUARIUS Edward Lifescience; May 2004, French, Ver. 4, Rev. C (2004).
Convention program of the Congress, "Extra-Renal Therapies in Intensive Care", Paris, Dec. 2003.
Brochure of a seminar, "Hamofiltrations—Seminer 2004", Saalfelden, Austria, May 2004.
C Ronco et al., Machines for continuous renal replacement therapies, from "Replacement of renal function by dialysis", $5^{th}$ edition, 2004, Kluwer Academic Publishers.
Notice of Opposition in the E.P.O., mail date is Nov. 27, 2013, along with an English-language translation thereof.
E.P.O. Brief Communication for EPO application 07707575.2, dated Jan. 15, 2015.

* cited by examiner

FIG. 3

|  | First Valve 11 | Second Valve 19 | Third Valve 34 |
|---|---|---|---|
| (A)CHD | ○(✕) | ○ | ✕(○) |
| (B)CHDF | ○(✕) | ○ | ✕(○) |
| (C)CHF | ○(✕) | ○ | ✕(○) |
| (D)ECUM | ✕ | ○ | ✕(○) |

○ : Open
✕ : Closed

FIG. 4

|  | First Supply Fluid Pump 10a | Second Supply Fluid Pump 10b | Blood Pump 22 | Filtrate Pump 29 |
|---|---|---|---|---|
| (A)CHD | ○ | × | ○ | ○ |
| (B)CHDF | ○ | ○ | ○ | ○ |
| (C)CHF | × | ○ | ○ | ○ |
| (D)ECUM | × | × | ○ | ○ |

○ : Operating

× : Stopped

BLOOD PURIFICATION APPARATUS AND BLOOD PURIFICATION CIRCUIT

TECHNICAL FIELD

The present invention relates to a blood purification apparatus and a blood purification circuit which are used to perform continuous blood purification methods.

BACKGROUND ART

Conventionally, for blood purification for, for example, renal function insufficiency patients, medical treatments by continuous blood purification methods such as Continuous Hemofiltration (CHF), Continuous Hemodia (CHD), and Continuous Hemodiafiltration (CHDF) have been performed. A blood perfusion speed of such a continuous blood purification method is lower than conventional hemodialysis, which can realize slower blood purification.

In the continuous blood purification methods, it is necessary to take a balance between (i) a flow rate of blood taken from a patient and (ii) a flow rate of blood returned to the patient and a replacement fluid injected into the patient. The balance is achieved by measuring respective used amounts of the dialysis fluid, the replacement fluid, and the filtrate, independently (refer to Patent Reference 1, for example).
Patent Reference 1: Japanese Patent No. 3180309

DISCLOSURE OF INVENTION

Problems that Invention is to Solve

However, the conventional continuous blood purification methods have the following problems. A circuit for independently flowing dialysis fluid, replacement fluid, and filtrate is complicated. Furthermore, a size of an apparatus performing such a continuous blood purification method is large. Still further, there is a high possibility of losing the above-mentioned balance, due to frequently-made erroneous differences between of actual used amounts and measured values of the respective fluids.

Moreover, the CHF, the CHD, the CHDF, and an Extracorporeal Ultrafiltration Method (ECUM) for removing only water from blood taken from a patient are currently performed by respective different circuits. Therefore, circuits dedicated to the CHF, the CHD, the CHDF, and the ECUM, respectively are necessary. Medical practitioners desire to perform all of the CHF, the CHD, the CHDF, and the ECUM using a single circuit.

The present invention addresses the above problems. It is an object of the present invention to provide a blood purification apparatus and a blood purification circuit, by which a circuit can be shared by different modes for performing respective continuous blood purification methods, a structure of an apparatus performing the continuous blood purification methods can be simplified, and all of the CHF, the CHD, the CHDF, and the ECUM can be performed.

Means to Solve the Problems

In accordance with an aspect of the present invention for achieving the object, there is provided a blood purification apparatus including: a first supply fluid channel having one end connected to a supply fluid container containing a supply fluid flowing in the first supply fluid channel; a first branched part connected to an other end of the first supply fluid channel; a second supply fluid channel having one end connected to the first branched part, and an other end connected to a hemofilter that purifies blood; and a third supply fluid channel having one end connected to the first branched part, and an other end connected to a blood channel in which the blood taken from a patient flows, wherein the second supply fluid channel has a first pump; and the third supply fluid channel has a second pump.

The blood purification apparatus may further include a measurement fluid channel having one end connected to the first branched part, and an other end connected to a supply fluid measurement container used for measuring an amount of the supply fluid flowing from the supply fluid container.

The first supply fluid channel may have a first opening-closing unit configured to (i) lead the supply fluid flowing in the first supply fluid channel, to the first branched part, or (ii) block the supply fluid, and the supply fluid contained in the supply fluid container may be led to the supply fluid measurement container due to head of fluid.

The blood purification apparatus may further include a filtrate channel (i) which has one end connected to the hemofilter, (ii) which includes a third pump, and (iii) in which a filtrate from the hemofilter flows; a second branched part connected to an other end of the filtrate channel; a discharged-fluid container connected to the second branched part and containing the filtrate flowing in the filtrate channel; and a filtrate measurement container connected to the second branched part and used for measuring an amount of the filtrate flowing from the hemofilter.

The blood purification apparatus may further include a control unit configured to (i) compare an amount of decrease in a fluid stocked in the supply fluid measurement container to an amount of increase in a filtrate stored in the filtrate measurement container, and (ii) control, based on a result of the comparison, an amount of increase or decrease in a filtrate filtered by the hemofilter.

The blood purification apparatus may further include a discharge channel having one end connected to the second branched part, and an other end connected to the discharged-fluid container, wherein the discharge channel includes a second opening-closing unit configured to (i) lead the filtrate flowing in the discharge channel to the discharged-fluid container, or (ii) block the filtrate.

The blood purification circuit may further include a discharge channel having one end connected to the second branched part, and an other end connected to the discharged-fluid container, wherein the discharge channel includes a second opening-closing unit configured to (i) lead the filtrate flowing in the discharge channel to the discharged-fluid container, or (ii) block the filtrate.

With the above structure, in the blood purification apparatus according to the present invention, a circuit can be shared by different modes for performing respective continuous blood purification methods, an apparatus performing the continuous blood purification methods has a simple structure, and all of the CHF, the CHD, the CHDF, and the ECUM can be performed. Furthermore, in blood purification using the CHDF, respective numbers of rotations of the first pump and the second pump can be controlled to change a ratio of the CHD to the CHF arbitrarily depending on a patient. As a result, the blood purification apparatus according to the present invention can perform high-accurate and effective hemodialysis.

In accordance with another aspect of the present invention for achieving the object, there is provided a blood purification circuit including: a first supply fluid channel having one end connected to a supply fluid container containing a supply fluid flowing in the first supply fluid channel; a first branched part connected to an other end of the first supply fluid channel; a second supply fluid channel having one end connected to the first branched part, and an other end connected to a hemofilter that purifies blood; and a third supply fluid channel having one end connected to the first branched part, and an other end connected to a blood channel in which the blood taken from a patient flows, wherein the second supply fluid channel has a first pump segment, and the third supply fluid channel has a second pump segment.

The blood purification circuit may further include a measurement fluid channel having one end connected to the first branched part, and an other end connected to a supply fluid measurement container used for measuring an amount of the supply fluid flowing from the supply fluid container.

The first supply fluid channel may have a first opening-closing unit configured to (i) lead the supply fluid flowing in the first supply fluid channel to the first branched part, or (ii) block the supply fluid, and the supply fluid contained in the supply fluid container is led to the supply fluid measurement container due to head of fluid.

The blood purification circuit may further include a filtrate channel (i) which has one end connected to the hemofilter, (ii) which includes a third pump segment, and (iii) in which a filtrate from the hemofilter flows; a second branched part connected to an other end of the filtrate channel; a discharged-fluid container connected to the second branched part and containing the filtrate flowing in the filtrate channel; and a filtrate measurement container connected to the second branched part and used for measuring an amount of the filtrate flowing from the hemofilter.

The blood purification circuit may further include a control unit configured to (i) compare an amount of decrease in a fluid stocked in the supply fluid measurement container to an amount of increase in a filtrate stored in the filtrate measurement container, and (ii) control, based on a result of the comparison, an increased-decreased amount of a filtrate filtered by the hemofilter.

Thereby, in the blood purification method according to the present invention, a circuit can be shared by different modes for performing respective continuous blood purification methods, an apparatus performing the continuous blood purification methods has a simple structure, and all of the CHF, the CHD, the CHDF, and the ECUM can be performed. Furthermore, in blood purification using the CHDF, respective numbers of rotations of a pump mounted on the first pump segment and a pump mounted on the second pump segment can be controlled to change a ratio of the CHD to the CHF arbitrarily depending on a patient. As a result, the blood purification method according to the present invention can perform high-accurate and effective hemodialysis.

Effects of the Invention

The present invention can provide a blood purification apparatus and a blood purification circuit, by which a circuit can be shared by different modes for performing respective continuous blood purification methods, an apparatus performing the continuous blood purification methods has a simple structure, and all of the CHF, the CHD, the CHDF, and the ECUM can be performed.

Furthermore, in blood purification using the CHDF, a ratio of the CHD to the CHF can be arbitrarily changed depending on a patient. As a result, the blood purification apparatus and the blood purification circuit according to the present invention can perform high-accurate and effective hemodialysis.

BRIEF DESCRIPTION OF DRAWINGS

FIG. 3 is a table indicating valve opening-closing information 540.
FIG. 4 is a table indicating pump operation information 560.

Figure 1:
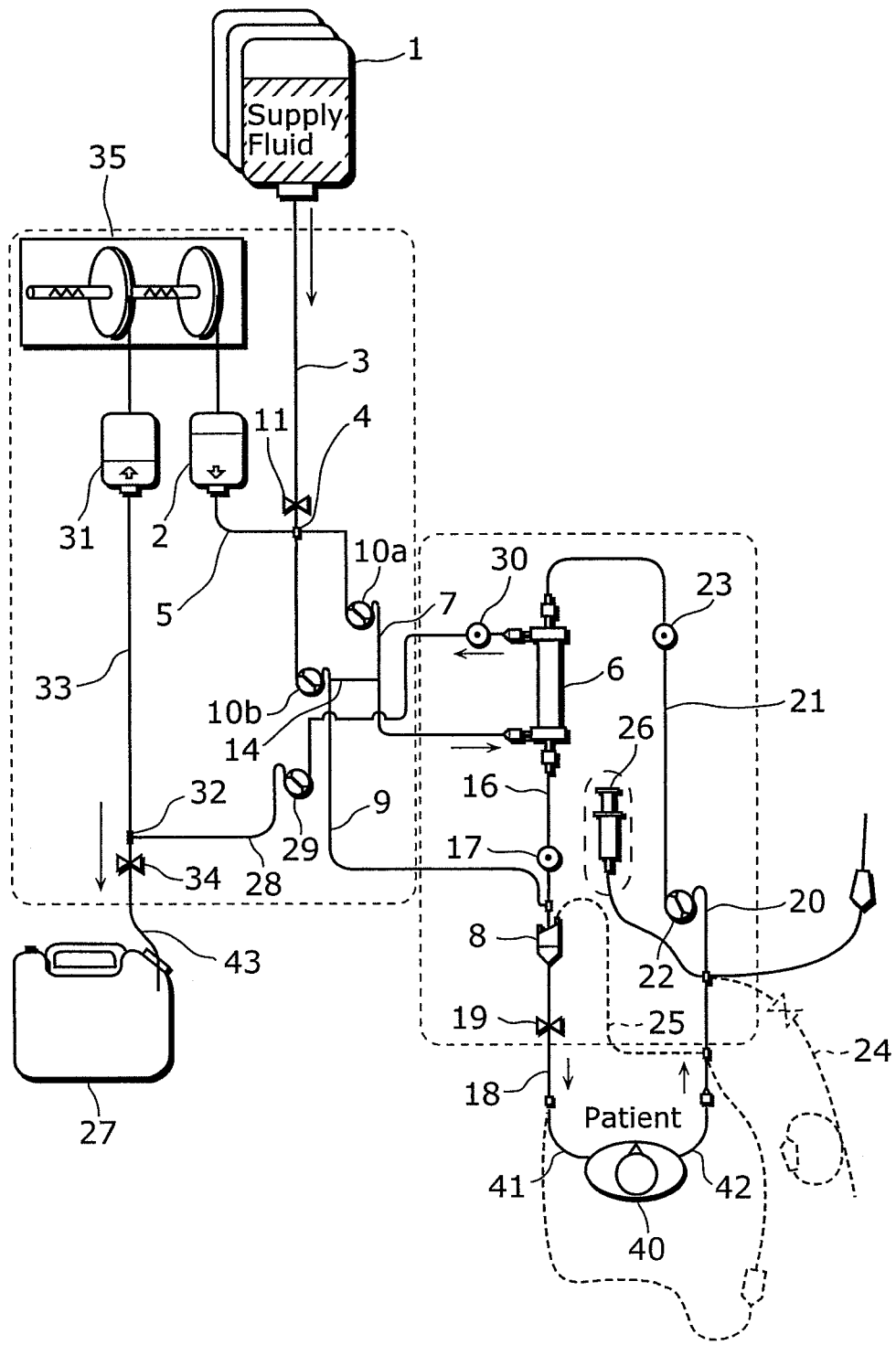
FIG. 1 is a diagram showing a structure of a blood purification circuit according to an embodiment of the present invention.

NUMERICAL REFERENCES 1 supply fluid container
2 supply fluid measurement container
3 first supply fluid channel
4 first branched part
5 supply fluid measurement fluid channel
6 dialyzer
7 second supply fluid channel
8 vapor-liquid separation chamber
9 third supply fluid channel
10a first supply fluid pump
10b second supply fluid pump
11 first valve
14 fourth supply fluid channel
16 vein side blood channel
17 first pressure sensor
18 inflow channel
19 second valve
20 artery side first blood channel
21 artery side second blood channel
22 blood pump
23 second pressure sensor
24 replacement fluid channel
25 third blood channel
26 syringe
27 discharged-fluid container
28 filtrate channel
29 filtrate pump
30 third pressure sensor
31 filtrate measurement container
33 filtrate measurement channel
34 third valve
35 balance detector
41 returning-side blood circuit
42 sending-side blood circuit
43 discharge channel
50 control apparatus
51 receiving unit
52 mode selection unit
53 valve control unit
54 valve opening-closing information storage unit
55 pump control unit
56 pump operation information storage unit

BEST MODE FOR CARRYING OUT THE INVENTION

The following describes the most preferred embodiment according to the present invention with reference to the drawings.

The blood purification apparatus according to the present embodiment includes a blood purification circuit and a control apparatus.

(Blood Purification Circuit)

Firstly, the blood purification circuit according to the present embodiment is described with reference to FIG. 1.

FIG. 1 is a block diagram showing a structure of the blood purification circuit according to the present embodiment.

The blood purification circuit according to the present embodiment is a circuit used in continuous blood purification methods. The blood purification circuit includes a supply fluid container 1, a supply fluid measurement container 2, a first supply fluid channel 3, a first branched part 4, a supply fluid measurement fluid channel 5, a dialyzer 6, a second supply fluid channel 7, a vapor-liquid separation chamber 8, a third supply fluid channel 9, a first supply fluid pump 10a, a second supply fluid pump 10b, a first valve 11, a vein side blood channel 16, a first pressure sensor 17, an inflow channel 18, a second valve 19, an artery side first blood channel 20, an artery side second blood channel 21, a blood pump 22, a second pressure sensor 23, a replacement fluid channel 24, a third blood channel 25, a syringe 26, a discharged-fluid container 27, a filtrate channel 28, a filtrate pump 29, a third pressure sensor 30, a filtrate measurement container 31, a filtrate measurement channel 33, a third valve 34, and a discharge channel 43.

The blood purification circuit according to the present embodiment is connected to a patient 40 via a returning-side blood circuit 41 and a sending-side blood circuit 42. FIG. 1 also shows a balance detector 35 that serves also as multiple measuring apparatuses.

The supply fluid container 1 is a container contained with a supply fluid. The supply fluid contained in the supply fluid container 1 is sterile enough to be supplied as a replacement fluid and also as a dialysis fluid. The supply fluid measurement container 2 is a container contained with a supply fluid having an amount required for continuous blood purification methods. The supply fluid container 1 and the supply fluid measurement container 2 are arranged sequentially in a direction of gravitational force, so that a supply fluid to be provided into the supply fluid measurement container 2 is supplied from the supply fluid container 1, due to head of fluid. The supply fluid measurement container 2 is a container for measuring an amount of a supply fluid flowing out from the supply fluid container 1. The first supply fluid channel 3 is a tubular channel in which a supply fluid flows. One end of the first supply fluid channel 3 is connected to the supply fluid container 1, and the other end of the first supply fluid channel 3 is connected to the first branched part 4. Here, each of fluid channels according to the present invention is a tubular channel like the first supply fluid channel 3. The first branched part 4 is a part connected to the other end of the first supply fluid channel 3. The supply fluid measurement fluid channel 5 is a channel for a supply fluid, and used, for example, to supply the supply fluid contained in the supply fluid container 1 to the supply fluid measurement container 2. One end of the supply fluid measurement fluid channel 5 is connected to the first branched part 4, and the other end of the supply fluid measurement fluid channel 5 is connected to the supply fluid measurement container 2.

The dialyzer 6 performs blood purification using blood filtering, blood dialysis, or filtering and dialysis. The second supply fluid channel 7 has one end connected to the first branched part 4, and the other end connected to the dialyzer 6. The second supply fluid channel 7 has a first supply fluid pump 10a. The second supply fluid channel 7 is a channel introducing a supply fluid supplied via the first supply fluid channel 3 from the supply fluid measurement container 2 into the dialyzer 6 using the first supply fluid pump 10a. The vapor-liquid separation chamber 8 is a container for removing gas from the blood channels, and contains blood. The third supply fluid channel 9 has one end connected to the first branched part 4, and the other end connected to the vein side blood channel 16. The third supply fluid channel 9 has a second supply fluid pump 10b. The third supply fluid channel 9 is a channel introducing a supply fluid supplied via the first supply fluid channel 3 from the supply fluid measurement container 2 into the vein side blood channel 16 using the second supply fluid pump 10b. The second supply fluid channel 7 and the third supply fluid channel 9 are connected to the first branched part 4. The supply fluid contained in the supply fluid container 1 is supplied to the supply fluid measurement container 2, due to head of fluid. Each of the first supply fluid pump 10a and the second supply fluid pump 10b leads, with a necessary amount or speed, the supply fluid contained in the supply fluid measurement container 2 to a downstream of the first supply fluid pump 10a or the second supply fluid pump 10b, such as the dialyzer 6 or the vein side blood channel 16, via the second supply fluid channel 7 or the third supply fluid channel 9.

The first valve 11 is provided in the first supply fluid channel 3. The first valve 11 is opened or closed, to lead the supply fluid flowing in the first supply fluid channel 3 into the first branched part 4 or block the supply fluid.

The vein side blood channel 16 means all channels of a blood circuit connecting the dialyzer 6 to a vein side connector (not shown) of the patient. The blood circuit connects a blood exit port of the dialyzer 6 to an upper part of the vapor-liquid separation chamber 8. With the structure, blood purified by the dialyzer 6 is led from the dialyzer 6 to the vapor-liquid separation chamber 8. The first pressure sensor 17 is provided in the vein side blood channel 16, and detects a pressure of a fluid flowing in the vein side blood channel 16. The inflow channel 18 has one end connected to the vapor-liquid separation chamber 8, and the other end connected to the returning-side blood circuit 41. The inflow channel 18 is a channel for fluid, and leads (i) the purified blood or (ii) the purified blood and a supply fluid, from the vapor-liquid separation chamber 8 to the patient 40. The second valve 19 is provided in the inflow channel 18. The second valve 19 leads a fluid flowing in the inflow channel 18 to the returning-side blood circuit 41, or blocks the fluid.

An artery side blood circuit means all channels of a blood circuit connecting the dialyzer 6 to an artery side connector (not shown) of the patient. The artery side blood circuit has the artery side first blood channel 20 and the artery side second blood channel 21. The artery side first blood channel 20 has one end connected to the sending-side blood circuit 42, and the other end connected to the artery side second blood channel 21. The artery side first blood channel 20 is a channel for blood, and leads blood flowing via the sending-side blood circuit 42 from the patient 40, to the dialyzer 6. A blood side pump segment is a part that is provided in the artery side second blood channel 21 and suitable for pumping. At the part, the blood pump 22 is provided. The artery side second blood channel 21 has one end connected to the blood channel 20, and the other end connected to the dialyzer 6. The artery side second blood channel 21 is a channel for blood, and leads blood flowing from the artery side first blood channel 20 to the dialyzer 6. The blood pump 22 is a pump provided in the blood side pump segment. The blood pump 22 supplies the blood of the patient 40 flowing via the sending-side blood circuit 42 and the artery side first blood channel 20, to the dialyzer 6. The second pressure sensor 23 is provided in the artery side second blood channel 21. The second pressure sensor 23 detects a pressure of blood flowing in the artery side second blood channel 21.

Solid lines shown in FIG. 1 are channels that are used during medical treatments, and broken lines are channels to be connected to the channels of the solid lines during priming.

During medical treatments, one end of the replacement fluid channel 24 to be used as a circuit for a replacement fluid is connected to the artery side first blood channel 20. During priming, the replacement fluid channel 24 is used as a channel that discharges a priming fluid (supply fluid stocked in the supply fluid container 1) flowing in the artery side first blood channel 20, to outside of the blood purification circuit.

During medical treatments, one end of the replacement fluid channel 25 that is used as a circuit for injecting a predetermined fluid including anticoagulant into blood is connected to the artery side first blood channel 20, and the other end of the replacement fluid channel 25 is connected to the syringe 26. During priming, the other end of the replacement fluid channel 25 is connected to the vapor-liquid separation chamber 8, and used as a bypass that leads the priming fluid directly to the replacement fluid channel 24 which serves as a discharge channel during priming, which can prevent a redundant pressure on the dialyzer 6. Here, the syringe 26 is contained with a predetermined fluid including anticoagulant and the like. An operation of a physician or the like or an injection apparatus injects the contained fluid to the blood flowing in the third blood channel 25.

During medical treatments, the returning-side blood circuit 41 and the sending-side blood circuit 42 are connected to the patient 40. During priming, the returning-side blood circuit 41 and the sending-side blood circuit 42 are not connected to the patient 40, but to a bypass line indirectly connected to the vapor-liquid separation chamber. The discharged-fluid container 27 is arranged vertically under the filtrate measurement container 31. The discharged-fluid container 27 is a container in which filtrate is stocked as a discharged fluid. The filtrate channel 28 is a channel for filtrate. One end of the filtrate channel 28 is connected to the dialyzer 6, and the other end of the filtrate channel 28 is connected to the second branched part 32. The discharge channel 43 is a channel for filtrate. One end of the discharge channel 43 is connected to the second branched part 32 provided in the filtrate channel 28, and the other end of the discharge channel 43 is connected to the discharged-fluid container 27. The filtrate pump 29 is provided in the filtrate channel 28. The filtrate pump 29 supplies filtrate generated by the dialyzer 6, to the discharged-fluid container 27. A filtrate pump segment is a part that is provided in the filtrate channel 28 and suitable for pumping. At the part, the filtrate pump 29 is provided. The third pressure sensor 30 is provided in the filtrate channel 28, to detect a pressure of a filtrate flowing in the filtrate channel 28. The filtrate measurement container 31 is a container in which a filtrate is stocked to be measured during continuous blood purification methods. The filtrate measurement channel 33 is a channel for filtrate. One end of the filtrate measurement channel 33 is connected to the second branched part 32 provided in the filtrate channel 28, and the other end of the filtrate measurement channel 33 is connected to the filtrate measurement container 31. The third valve 34 is provided in the discharge channel 43. The third valve 34 leads the filtrate flowing in the filtrate measurement channel 33 to the discharged-fluid container 27, or blocks the filtrate.

The balance detector 35 detects whether or not there is a balance between (i) an amount of decrease in the supply fluid contained in the supply fluid measurement container 2 and (ii) an amount of increase in the filtrate stocked in the filtrate measurement container 31. The balance detector 35 will be described in more detail in the description for the control apparatus 50.

The second supply fluid channel 7 has a supply fluid side pump segment as a part suitable for pumping. In the supply fluid side pump segment, the first supply fluid pump 10a is provided. Likewise, the third supply fluid channel 9 has a supply fluid side pump segment as a part suitable for pumping. In the supply fluid side pump segment, the second supply fluid pump 10b is provided.

(Control Apparatus)

Figure 2:
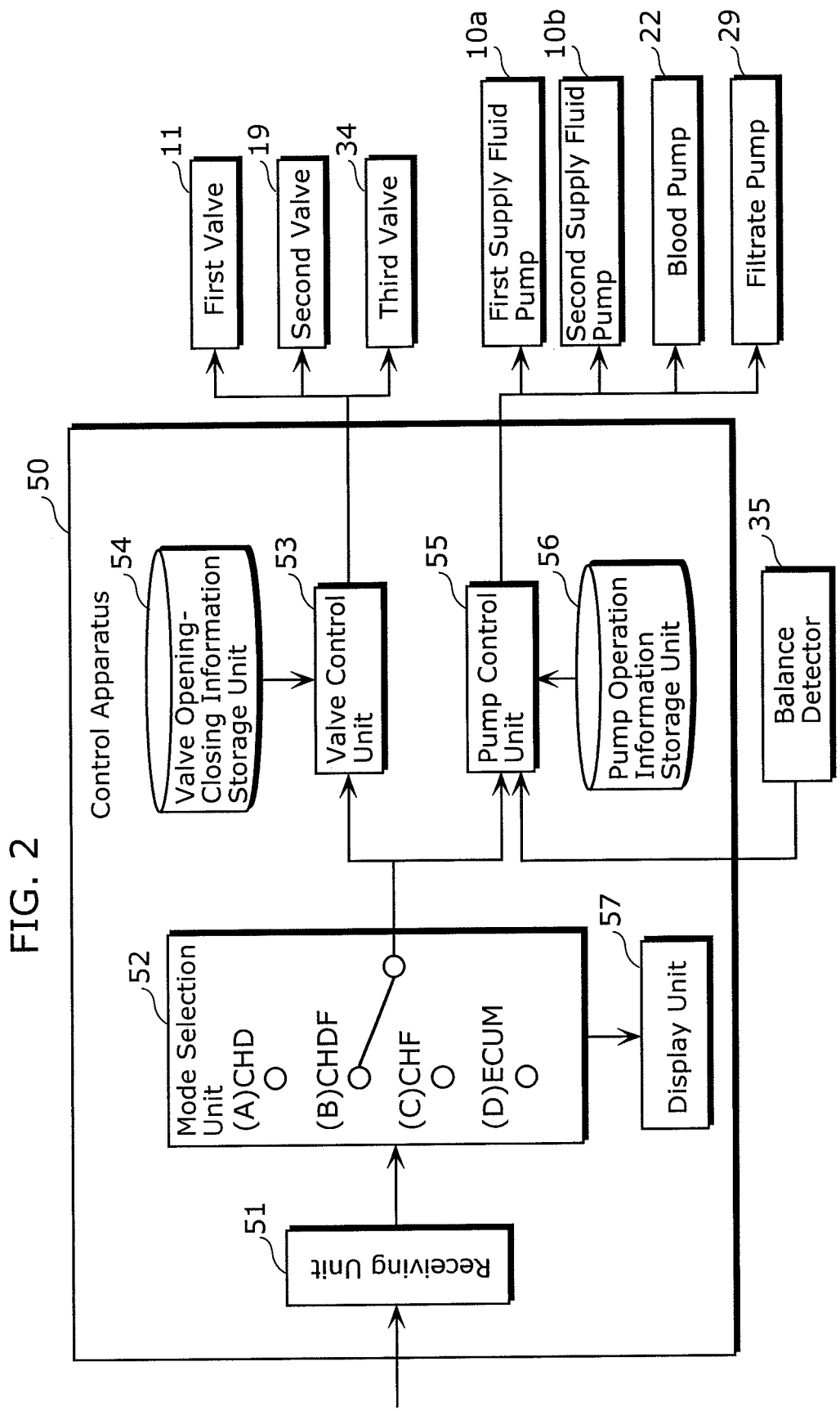
FIG. 2 is a block diagram of a control apparatus 50.

Next, the description is given for the control apparatus 50 that controls a flow of each fluid flowing in the blood purification circuit according to the present embodiment, with reference to FIG. 2.

FIG. 2 is a block diagram of the control apparatus 50. The control apparatus 50 is an apparatus that controls a flow of each fluid flowing in the blood purification circuit according to the present embodiment. The control apparatus 50 includes a receiving unit 51, a mode selection unit 52, a valve control unit 53, a valve opening-closing information storage unit 54, a pump control unit 55, a pump operation information storage unit 56, and a display unit 57.

From a user such as a physician, the receiving unit 51 receives mode information for specifying a continuous blood purification mode performed using the blood purification circuit. The mode selection unit 52 selects one of multiple continuous blood purification modes, based on the mode information received by the receiving unit 51. There are four kinds of modes: a CHD mode (A), a CHDF mode (B), a CHF mode (C), and an ECUM mode (D). Before performing any one of the four modes, a pre-processing is necessary to clean the channels for respective fluids and fill supply fluids, for example. Hereinafter, the pre-processing is called a priming mode. Since the CHD, the CHDF, the CHF, and the ECUM have been explained in the above Background Art, the explanation is therefore not repeated herein again.

Based on the valve opening-closing information 540 stored in the valve opening-closing information storage unit 54, the valve control unit 53 controls opening and closing operations of a valve according to the mode selected by the mode selection unit 52. In the valve opening-closing information storage unit 54, valve opening-closing information 540 for designating whether each valve is opened or closed is stored for each mode.

FIG. 3 shows the valve opening-closing information 540. As shown in FIG. 3, in the case where the CHD mode (A) is to be performed, the second valve 19 is opened and the third valve 34 is closed. In each of cases of the CHDF mode (B), the CHF mode (C), and the ECUM mode (D), each of the second valve 19 and the third valve 34 is opened or closed based on the valve opening-closing information 540 shown in FIG. 3.

Based on the pump operation information 560 stored in the pump operation information storage unit 56, the pump control unit 55 controls operations of driving a pump corresponding to the mode selected by the mode selection unit 52. In the pump operation information storage unit 56, the pump operation information 560 for designating whether each pump is to be operated or stopped is stored for each mode.

FIG. 4 shows the pump operation information 560. As shown in FIG. 4, in the case where the CHD mode (A) is to be performed, the first supply fluid pump 10a, the blood pump 22, and the filtrate pump 29 are operated. In each of the cases of the CHDF mode (B), the CHF mode (C), and the ECUM mode (D), each of the first supply fluid pump 10a, the second supply fluid pump 10b, the blood pump 22, and the filtrate pump 29 is operated or stopped, based on the pump operation information 560 shown in FIG. 4.

When the mode selected by the mode selection unit 52 is the CHDF mode (B), the pump control unit 55 controls the number of rotations of each of the first supply fluid pump 10a and the second supply fluid pump 10b, according to information regarding a ratio of the CHD to the CHF inputted by the user via the receiving unit 51.

When the balance detector 35 detects that there is no balance between (i) an amount of decrease in the supply fluid contained in the supply fluid measurement container 2 and (ii) an amount of increase in filtrate stocked in the filtrate measurement container 31, the pump control unit 55 controls all or a part of the first supply fluid pump 10a, the second supply fluid pump 10b, the blood pump 22, and the filtrate pump 29, so that a balance is established between the amount of decrease and the amount of increase. Here, the detection of the balance detector 35 is performed by detecting the amount of decrease in the supply fluid and the amount of increase in the filtrate at a predetermined timing in a predetermined time period.

According to a mode corresponding to mode information received by the receiving unit 51, the display unit 57 displays information indicating in which channel from among the second supply fluid channel 7 and the third supply fluid channel 9 of the blood purification circuit the supply fluid flows.

Next, operations of the control apparatus 50 are described.

After the above-described blood purification circuit is set to the patient, from a user such as a physician, the receiving unit 51 receives mode information for specifying a mode to be performed, from among the CHD mode (A), the CHDF mode (B), the CHF mode (C), and the ECUM mode (D). When the receiving unit 51 receives the mode information, the mode selection unit 52 notifies operation start information to the valve control unit 53 and the pump control unit 55. The valve control unit 53 opens the first valve 11 during a first predetermined time period. The valve control unit 53 makes the first valve 11 keep opened during the first predetermined time period, so that a supply fluid having a predetermined amount contained in the supply fluid container 1 is supplied to the supply fluid measurement container 2 due to head of fluid. Thereby, the supply fluid of the predetermined amount is provided to the supply fluid measurement container 2.

After that, the valve control unit 53 closes the first valve 11. Here, the second valve 19 is kept opened. The pump control unit 55 operates the first supply fluid pump 10a, the second supply fluid pump 10b, the blood pump 22, and the filtrate pump 29 during a second predetermined time period, so that the supply fluid flows through these fluid channels.

After passing the second predetermined time period, the mode selection unit 52 notifies the valve control unit 53 and the pump control unit 55 of the mode information received by the receiving unit 51.

The valve control unit 53 controls opening and closing of the second valve 19 and the third valve 34, according to the information corresponding to the notified mode information regarding the valve opening-closing information 540 stored in the valve opening-closing information storage unit 54. For example, when the mode indicated by the mode information is the CHD mode (A), the valve control unit 53 opens the second valve 19, and opens and closes the third valve 34. For example, when the mode indicated by the mode information is the CHDF mode (B), the valve control unit 53 opens the second valve 19, and opens and closes the third valve 34. Here, basically, the second valve 19 is kept opened during the blood purification, but closed during troubles such as detection of air bubbles in the vapor-liquid separation chamber 8.

The pump control unit 55 controls operations of the first supply fluid pump 10a, the second supply fluid pump 10b, the blood pump 22, and the filtrate pump 29, according to the information corresponding to the notified mode information regarding the pump operation information 560 stored in the pump operation information storage unit 56. For example, when the mode indicated by the mode information is the CHD mode (A), the pump control unit 55 operates the first supply fluid pump 10a, the blood pump 22, and the filtrate pump 29. For example, when the mode indicated by the mode information is the ECUM mode (D), the pump control unit 55 operates the blood pump 22 and the filtrate pump 29, and stops the first supply fluid pump 10a and the second supply fluid pump 10b.

According to a mode corresponding to the mode information received by the receiving unit 51, the display unit 57 displays information indicating in which channel from among the second supply fluid channel 7 and the third supply fluid channel 9 of the blood purification circuit the supply fluid flows. In more detail, when the CHD mode (A) is to be performed, the display unit 57 displays information indicating that the supply fluid flows in the second supply fluid channel 7 but does not flow in the third supply fluid channel 9. When the CHDF mode (B) is to be performed, the display unit 57 displays information indicating that the supply fluid flows both in the second supply fluid channel 7 and the third supply fluid channel 9. When the CHF mode (C) is to be performed, the display unit 57 displays information indicating that the supply fluid flows in the third supply fluid channel 9 but does not flow in the second supply fluid channel 7. When the ECUM mode (D) is to be performed, the display unit 57 displays information indicating that the supply fluid flows neither in the second supply fluid channel 7 nor the third supply fluid channel 9.

As described above, according to the present invention, the single blood purification circuit and the single control apparatus 50 can perform all modes of the continuous blood purification methods, such as the CHD mode (A), the CHDF mode (B), the CHF mode (C), and the ECUM mode (D). Therefore, apparatuses dedicated to these modes, respectively, are not necessary. Furthermore, the supply fluid contained in the supply fluid container 1 is used as a replacement fluid and a dialysis fluid, so that the supply fluid of a predetermined amount is provided to the supply fluid measurement container 2 to be used in any of the modes. Since the same supply fluid can be used as the replacement fluid and the dialysis fluid, the circuit for performing the continuous blood purification methods can be simplified, and a size of the apparatus for performing the continuous blood purification methods can be reduced. As a result, it is possible to easily establish a balance between (i) a flow amount of a fluid taken from the patient and (ii) a flow amount of a fluid supplied to the patient. Still further, a supply fluid channel in which a supply fluid flows is branched, and each of the branched supply fluid channels has a pump. One of the branched supply fluid channels is functioned as a channel for dialysis fluid, and the other channel is functioned as a channel for a replacement fluid. Thereby, flow amounts of the dialysis fluid and the replacement fluid can be independently controlled with high accuracy. This makes it possible to arbitrarily change a ratio of the CHD to the CHF depending on a patient, when blood purification is performed by the CHDF. As a result, blood dialysis can be performed with high accuracy and efficiently.

Next, the balance detector 35 shown in FIG. 1 is described in more detail.

Figure 5:
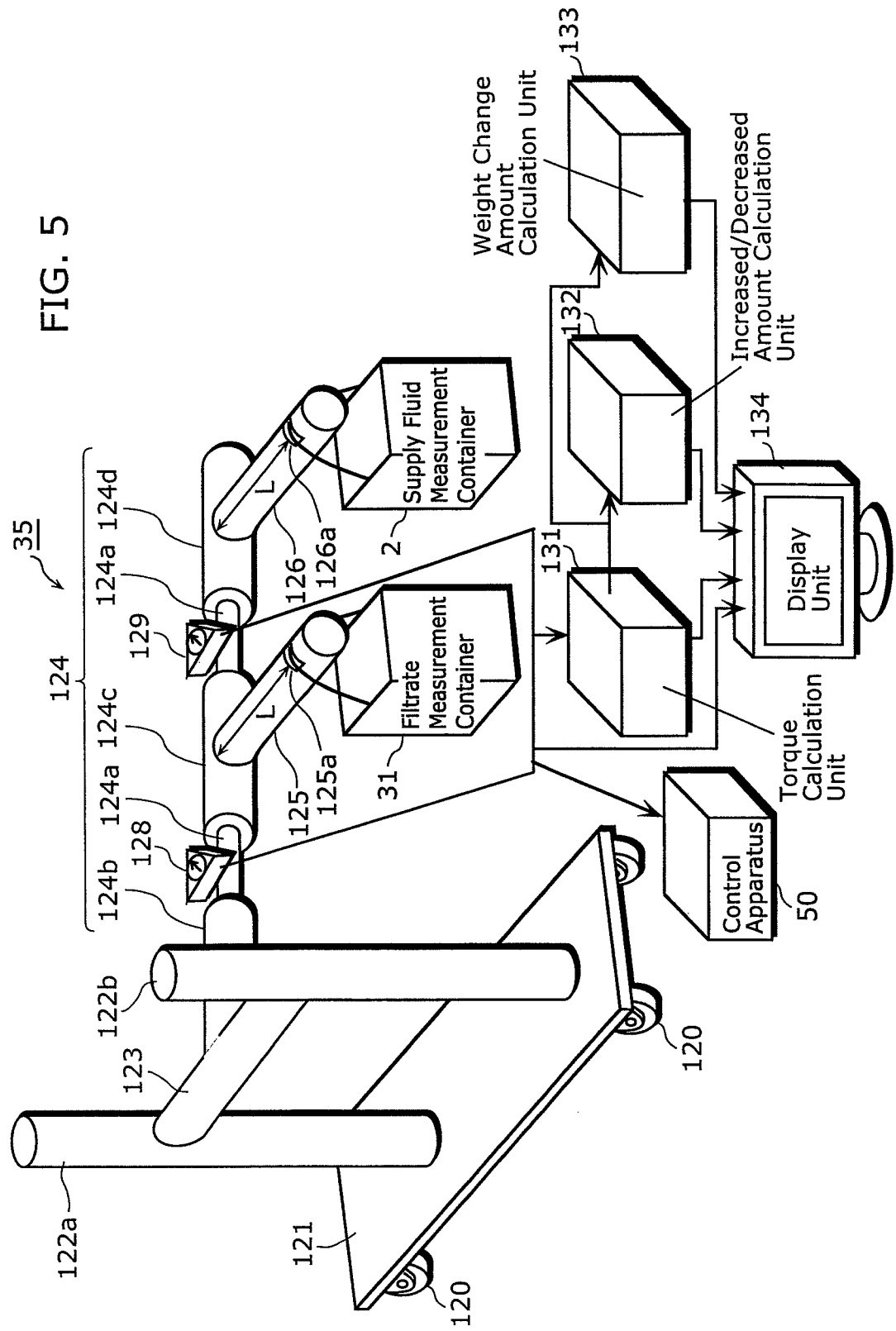
FIG. 5 is a diagram showing a structure of a balance detector 35.

As described above, the balance detector 35 detects whether or not there is a balance between (i) an amount of decrease in the supply fluid contained in the supply fluid measurement container 2 and (ii) an amount of increase in the filtrate stocked in the filtrate measurement container 31. FIG. 5 shows a structure of the balance detector 35. As shown in FIG. 5, the balance detector 35 includes a base 121, a pillar 122a, a pillar 122b, a bridging beam 123, a first bar-shaped member 124, a filtrate bar-shaped member 125, a supply-fluid bar-shaped member 126, a first torque sensor 128, a second torque sensor 129, a torque calculation unit 131, an increased/decreased amount calculation unit 132, a weight change amount calculation unit 133, and a display unit 134. Here, FIG. 5 also shows the control apparatus 50, the supply fluid measurement container 2, and the filtrate measurement container 31.

The base 121 is a board having casters 120 under the board. The base 121 can move using the casters 120. The pillar 122a and the pillar 122b are bars fixed on the base 121, being arranged orthogonal to the base 121. There is a predetermined distance between the pillar 122a and the pillar 122b. The bridging beam 123 is a bar fixed to the pillar 122a and the pillar 122b horizontally at a predetermined height near to the base 121 more than top parts of the pillar 122a and the pillar 122b. The bridging beam 123 bridges the gap between the pillar 122a and the pillar 122b, thereby supporting the pillar 122a and the pillar 122b to stand erect on the base 121.

The first bar-shaped member 124 is a bar having one end connected to the middle of the bridging beam 123 and the other end connected to nothing, so that the first bar-shaped member 124 is arranged orthogonal to the bridging beam 123 and also in parallel to the base 121, namely, horizontally. As shown in FIG. 5, the first bar-shaped member 124 includes: a central axis 124a; and a first external cylinder 124b, a second external cylinder 124c, and a third external cylinder 124d each of which has the central axis 124a as an axis and covers the central axis 124a. A length of each of the first external cylinder 124b, the second external cylinder 124c, and the third external cylinder 124d is shorter than one third of a length of the central axis 124a. A diameter of a central axis hole of each of the first external cylinder 124b, the second external cylinder 124c, and the third external cylinder 124d is enough for insertion of the central axis 124a. The first external cylinder 124b, the second external cylinder 124c, and the third external cylinder 124d are arranged in a direction of the central axis 124a spaced apart, contacting and covering the central axis 124a. Therefore, the first bar-shaped member 124 has two parts that are thinner than other parts in a direction of the central axis 124a. Here, the first external cylinder 124b is fixed to the bridging beam 123. The first external cylinder 124b, the second external cylinder 124c, and the third external cylinder 124d are sequentially arranged in an order of nearer to the bridging beam 123.

The filtrate bar-shaped member 125 is horizontally orthogonal to the first bar-shaped member 124, and is fixed to the second external cylinder 124c of the first bar-shaped member 124. At a position having a distance L from where the filtrate bar-shaped member 125 is connected to the first bar-shaped member 124, there is a concave holding unit 125a for holding the filtrate measurement container 31. The supply-fluid bar-shaped member 126 is a bar horizontally orthogonal to the first bar-shaped member 124, and is fixed to the third external cylinder 124d of the first bar-shaped member 124. At a position having a distance L from where the supply-fluid bar-shaped member 126 is connected to the first bar-shaped member 124, there is a concave holding unit 126a for holding the supply fluid measurement container 2. Here, as shown in FIG. 5, each of the filtrate bar-shaped member 125 and the supply-fluid bar-shaped member 126 is arranged to the same side of a vertical plane including the first bar-shaped member 124. Moreover, each of the supply fluid measurement container 2 and the filtrate measurement container 31 has a handle on the top of the container. The supply fluid measurement container 2 is held using the handle placed on the holding unit 126a of the supply-fluid bar-shaped member 126. The filtrate measurement container 31 is held using the handle placed on the holding unit 125a of the filtrate bar-shaped member 125.

The first torque sensor 128 is provided to a part of the central axis 124a between the first external cylinder 124b and the second external cylinder 124c of the first bar-shaped member 124. The first torque sensor 128 detects a sum of (i) a torque of the holding unit 125a formed in the filtrate bar-shaped member 125 (hereinafter, referred to as a "torque around the second external cylinder 124c") and (ii) a torque of the holding unit 126a formed in the supply-fluid bar-shaped member 126 (hereinafter, referred to as a "torque around the third external cylinder 124d"). The second torque sensor 129 is provided to a part of the central axis 124a between the second external cylinder 124c and the third external cylinder 124d of the first bar-shaped member 124. The second torque sensor 129 detects the torque around the third external cylinder 124d.

The torque calculation unit 131 calculates the torque around the second external cylinder 124c, based on detection results detected by the first torque sensor 128 and the second torque sensor 129. In more detail, the torque calculation unit 131 calculates the torque around the second external cylinder 124c, by subtracting the detected value of the first torque sensor 128 by the detected value of the second torque sensor 129.

The increased/decreased amount calculation unit 132 calculates an increased/decreased amount of a weight of each of the supply fluid measurement container 2 and the filtrate measurement container 31 in comparison with an initial amount, based on the torque around the second external cylinder 124c and the torque around the third external cylinder 124d that are detected by the second torque sensor 129 and the torque calculation unit 131, respectively. That is, the increased/decreased amount calculation unit 132 calculates (i) a total amount of a filtrate that has actually been discharged and (ii) a total amount of a supply fluid that has actually been used. The increased/decreased amount calculation unit 132 calculates the total amount of the filtrate that has actually been discharged, by dividing (i) an amount of increase of the torque around the second external cylinder 124c which is increased from the initial amount and calculated by the torque calculation unit 131 by (ii) the distance L. In addition, the increased/decreased amount calculation unit 132 calculates the total amount of the supply fluid that has actually been used, by dividing (i) an amount of decrease of the torque around the third external cylinder 124d which is decreased from the initial amount and calculated by the second torque calculation unit 129 by (ii) the distance L.

The increased/decreased amount calculation unit 132 calculates a temporal amount of change in a weight of each of the supply fluid measurement container 2 and the filtrate measurement container 31, in other words, a flow amount of a discharged filtrate and a flow amount of a used supply fluid, based on the torque around the second external cylinder 124c and the torque around the third external cylinder 124d that are detected by the second torque sensor 129 and the torque calculation unit 131, respectively. The flow amount of the discharged filtrate is a value calculated by dividing (i) an amount of increase in a total amount of a filtrate corresponding to a temporal change by (ii) a relative density of the filtrate. The flow amount of the used supply fluid is a value calculated by dividing (i) an amount of decrease in a total amount of a supply fluid corresponding to a temporal change by (ii) a relative density of the supply fluid. Here, the weight change amount calculation unit 133 calculates a temporal amount of change in the torque around the second external cylinder 124c calculated by the torque calculation unit 131, then divides the calculated value by the distance L, and then further divides the divided value by a relative density of an estimated filtrate, thereby obtaining the flow amount of the discharged filtrate. In addition, the weight change amount calculation unit 133 calculates a temporal amount of change in the torque around the third external cylinder 124d detected by the second torque sensor 129, then divides the calculated value by the distance L, and then further divides the divided value by a relative density of a supply fluid, thereby obtaining the flow amount of the used supply fluid.

Here, the weight change amount calculation unit 133 determines whether or not the calculated temporal amount of change in the torque around the second external cylinder 124c is "constant". When the calculated temporal amount of change in the torque around the second external cylinder 124c is constant, the temporal amount of decrease in the supply fluid is equal to the temporal amount of increase in the filtrate, so that a balance is established between (i) a flow amount of blood taken from the patient 40 and (ii) a total flow amount of blood returning to the patient 40 and a supply fluid (replacement fluid) injected to the patient 40. Here, the "constant" may be "within a predetermined range".

The display unit 134 displays respective detection results detected by the first torque sensor 128 and the second torque sensor 129, and respective results calculated by the torque calculation unit 131, the increased/decreased amount calculation unit 132, and the weight change amount calculation unit 133.

When the weight change amount calculation unit 133 determines that the temporal amount of change in the torque around the second external cylinder 124c is not "constant", the pump control unit 55 controls all or a part of the first supply fluid pump 10a, the second supply fluid pump 10b, the blood pump 22, and the filtrate pump 29 so that the above temporal amount of change becomes "constant". Thereby, a balance is established between (i) an amount of decrease in the supply fluid contained in the supply fluid measurement container 2 and (ii) an amount of increase in the filtrate stocked in the filtrate measurement container 31. That is, there is a balance between (i) a flow amount of blood taken from the patient 40 and (ii) a total flow amount of blood returning to the patient 40 and a supply fluid (replacement fluid) injected into the patient 40.

INDUSTRIAL APPLICABILITY

The blood purification apparatus and the blood purification circuit according to the present invention are useful as an apparatus and a circuit that perform continuous blood purification methods.

What is claimed is:

1. a blood purification apparatus comprising:
a first supply fluid channel having one end connected to a supply fluid container containing a supply fluid flowing in said first supply fluid channel;
a first branched part connected to an other end of said first supply fluid channel;
a second supply fluid channel having one end connected to said first branched part, and an other end connected to a hemofilter that purifies blood, said second supply fluid channel having a first pump;
a third supply fluid channel having one end connected to said first branched part, and an other end connected to a blood channel in which blood taken from a patient flows, said third supply fluid channel having a second pump;
a supply fluid measurement container having one end connected to said first branched part, and used for measuring an amount of the supply fluid flowing from said supply fluid container;
a filtrate channel (i) which has one end connected to said hemofilter, (ii) which includes a third pump, and (iii) in which a filtrate from said hemofilter flows;
a second branched part connected to an other end of said filtrate channel;
a discharged-fluid container connected to said second branched part and containing the filtrate flowing in said filtrate channel;
a filtrate measurement container connected to said second branched part, and used for measuring an amount of the filtrate flowing from said hemofilter;
a balance detector which detects whether or not there is a balance between (i) an amount of decrease in a supply fluid contained in said supply fluid measurement container and (ii) an amount of increase in a filtrate contained in said filtrate measurement container, and which measures both an amount of the filtrate in said filtrate measurement container and an amount of the supply fluid in said supply fluid measurement container, said balance detector comprising a weight change amount calculation unit that calculates a flow amount of the filtrate and a flow amount of the supply fluid, and an increased/decreased amount calculation unit that calculates the amount of filtrate in said filtrate measurement container and the amount of the supply fluid in said supply fluid measurement container; and
a control unit configured to control said first pump, said second pump, and said third pump, to maintain a balance between (i) the supply fluid contained in said supply fluid measurement container and the filtrate contained in said filtrate measurement container, and (ii) an amount of decrease in the supply fluid in said supply fluid measurement container and an amount of increase in the filtrate stocked in said filtrate measurement container based on a determination made by said weight change amount calculation unit.

2. The blood purification apparatus according to claim 1, wherein said first supply fluid channel has a first opening-closing unit configured to (i) lead the supply fluid flowing in said first supply fluid channel to said first branched part, and (ii) block the supply fluid, and
wherein the supply fluid contained in said supply fluid container is led to said supply fluid measurement container due to a head of fluid.

3. The blood purification apparatus according to claim 2, further comprising:
a discharge channel having one end connected to said second branched part, and an other end connected to said discharged-fluid container,
wherein said discharge channel includes a second opening-closing unit configured to (i) lead the filtrate flowing in said discharge channel to said discharged-fluid container, and (ii) block the filtrate.

4. The blood purification apparatus according to claim 3, wherein said control unit further includes a receiving unit configured to receive mode information, the mode information specifying which mode among a plurality of continuous blood purification modes is to be performed, and wherein said control unit is configured to further control, based on the mode information, opening and closing of each of said first opening-closing unit and said second opening-closing unit.

5. A blood purification circuit comprising:
a first supply fluid channel having one end connected to a supply fluid container containing a supply fluid flowing in said first supply fluid channel;
a first branched part connected to an other end of said first supply fluid channel;
a second supply fluid channel having one end connected to said first branched part, and an other end connected to a hemofilter that purifies blood, said second supply fluid channel having a first pump segment;
a third supply fluid channel having one end connected to said first branched part, and an other end connected to a blood channel in which blood taken from a patient flows, said third supply fluid channel having a second pump segment;
a supply fluid measurement container having one end connected to said first branched part, and used for measuring an amount of the supply fluid flowing from said supply fluid container;
a filtrate channel (i) which has one end connected to said hemofilter, (ii) which includes a third pump segment, and (iii) in which a filtrate from said hemofilter flows;
a second branched part connected to an other end of said filtrate channel;
a discharged-fluid container connected to said second branched part and containing the filtrate flowing in said filtrate channel;
a filtrate measurement container connected to said second branched part, and used for measuring an amount of the filtrate flowing from said hemofilter;
a balance detector which detects whether or not there is a balance between (i) an amount of decrease in a supply fluid contained in said supply fluid measurement container and (ii) an amount of increase in a filtrate contained in said filtrate measurement container, and which measures both an amount of the filtrate in said filtrate measurement container and an amount of the supply fluid in said supply fluid measurement container, said balance detector comprising a weight change amount calculation unit that calculates a flow amount of the filtrate and a flow amount of the supply fluid, and an increased/decreased amount calculation unit that calculates the amount of filtrate in said filtrate measurement container and the amount of the supply fluid in said supply fluid measurement container; and
a control unit configured to control said first pump segment, said second pump segment, and said third pump segment, to maintain a balance between (i) the supply fluid contained in said supply fluid measurement container and the filtrate contained in said filtrate measurement container, and (ii) an amount of decrease in the supply fluid in said supply fluid measurement container and an amount of increase in the filtrate stocked in said filtrate measurement container based on a determination made by said weight change amount calculation unit.

6. The blood purification circuit according to claim 5,
wherein said first supply fluid channel has a first opening-closing unit configured to (i) lead the supply fluid flowing in said first supply fluid channel to said first branched part, and (ii) block the supply fluid, and
the supply fluid contained in said supply fluid container is led to said supply fluid measurement container due to head of fluid.

7. The blood purification circuit according to claim 6, further comprising:
a discharge channel having one end connected to said second branched part, and an other end connected to said discharged-fluid container,
wherein said discharge channel includes a second opening-closing unit configured to (i) lead the filtrate flowing in said discharge channel to said discharged-fluid container, and (ii) block the filtrate.

8. The blood purification apparatus according to claim 1,
wherein said control unit includes a receiving unit configured to receive mode information, the mode information specifying which mode among a plurality of continuous blood purification modes is to be performed,
wherein said control unit is configured to control operation and stoppage of each of said first pump segment and said second pump segment based on the mode information, and
wherein said control unit is configured to:
stop the first pump and operate the second pump based on mode information for specifying Continuous Hemofiltration (CHF) to be performed;
operate the first pump and stop the second pump based on mode information for specifying Continuous Hemodia (CHD) to be performed; and
operate the first pump and operate the second pump based on mode information for specifying Continuous Hemodiafiltration (CHDF) to be performed.

9. The blood purification circuit according to claim 5,
wherein said control unit includes a receiving unit configured to receive mode information, the mode information specifying which mode among a plurality of continuous blood purification modes is to be performed,
wherein said control unit is configured to control operation and stoppage of each of said first pump segment and said second pump segment based on the mode information, and
wherein said control unit is configured to:
stop the first pump segment and operate the second pump segment based on mode information for specifying Continuous Hemofiltration (CHF) to be performed;
operate the first pump segment and stop the second pump segment based on mode information for specifying Continuous Hemodia (CHD) to be performed; and
operate the first pump segment and operate the second pump segment based on mode information for specifying Continuous Hemodiafiltration (CHDF) to be performed.

10. The blood purification apparatus according to claim 1,
wherein said balance detector includes:
a pillar;
a bar-shaped member having one fixed end fixed to said pillar and a free end;
a supply-fluid bar-shaped member for holding said supply fluid measurement container and a filtrate bar-shaped member for holding said filtrate measurement container, said supply-fluid bar-shaped member and said filtrate bar-shaped member being provided on a surface of said bar-shaped member and being provided to respective two positions along a longitudinal direction of said bar-shaped member;
a first torque sensor provided on a part between the respective two positions on said bar-shaped member, and said first torque sensor configured to detect a torque of one of said supply-fluid bar-shaped member and said filtrate bar-shaped member, the one being provided proximate the free end of said bar-shaped member;

a second torque sensor provided on a part between (a) the respective two positions on said bar-shaped member and (b) the fixed end of said bar-shaped member, and said second torque sensor configured to detect a sum of (i) a torque of said supply-fluid bar-shaped member and (ii) a torque of said filtrate bar-shaped member.

11. The blood purification circuit according to claim 5, wherein said balance detector includes:

a pillar;

a bar-shaped member having one fixed end fixed to said pillar and a free end;

a supply-fluid bar-shaped member for holding said supply fluid measurement container and a filtrate bar-shaped member for holding said filtrate measurement container, said supply-fluid bar-shaped member and said filtrate bar-shaped member being provided on a surface of said bar-shaped member and being provided to respective two positions along a longitudinal direction of said bar-shaped member;

a first torque sensor provided on a part between the respective two positions on said bar-shaped member, and said first torque sensor configured to detect a torque of one of said supply-fluid bar-shaped member and said filtrate bar-shaped member, the one being provided proximate the free end of said bar-shaped member;

a second torque sensor provided on a part between (a) the respective two positions on said bar-shaped member and (b) the fixed end of said bar-shaped member, and said second torque sensor configured to detect a sum of (i) a torque of said supply-fluid bar-shaped member and (ii) a torque of said filtrate bar-shaped member.

\* \* \* \* \*